US006660715B2

(12) United States Patent
Klibanov

(10) Patent No.: US 6,660,715 B2
(45) Date of Patent: Dec. 9, 2003

(54) NONAQUEOUS SOLUTIONS AND SUSPENSIONS OF MACROMOLECULES FOR PULMONARY DELIVERY

(75) Inventor: Alexander M. Klibanov, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/443,716

(22) Filed: Nov. 19, 1999

(65) Prior Publication Data

US 2003/0035775 A1 Feb. 20, 2003

Related U.S. Application Data

(60) Provisional application No. 60/109,254, filed on Nov. 19, 1998, and provisional application No. 60/116,860, filed on Jan. 22, 1999.

(51) Int. Cl.$^7$ .......................... A61K 31/00; A61K 38/00
(52) U.S. Cl. ............................................. 514/2; 514/44
(58) Field of Search ........................................ 514/2, 44

(56) References Cited

U.S. PATENT DOCUMENTS

| 3,632,743 A | | 1/1972 | Geller et al. |
|---|---|---|---|
| 4,855,233 A | | 8/1989 | Gancet et al. |
| 5,006,343 A | | 4/1991 | Benson et al. |
| 5,230,884 A | | 7/1993 | Evans et al. |
| 5,292,499 A | * | 3/1994 | Evans et al. |
| 5,451,569 A | | 9/1995 | Wong et al. |
| 5,474,983 A | | 12/1995 | Kuna et al. |
| 5,536,444 A | | 7/1996 | Hettche et al. |
| 5,618,786 A | * | 4/1997 | Roosdorp et al. |
| 5,654,007 A | | 8/1997 | Johnson et al. |
| 5,709,902 A | | 1/1998 | Lloyd et al. |
| 5,726,154 A | | 3/1998 | Baudys et al. |

FOREIGN PATENT DOCUMENTS

| EP | WO 91/04054 | * | 9/1990 |
|---|---|---|---|
| EP | WO 93/04671 | * | 8/1992 |
| WO | WO 90/09167 | | 8/1990 |
| WO | WO 94/08599 | | 4/1994 |
| WO | WO 97/36574 A1 | | 10/1997 |

OTHER PUBLICATIONS

Adlercreutz, "On the importance of the support material for enzymatic synthesis in organic media. Support effects at controlled water activity," *Eur J Biochem* 199:609–14 (1991).
Affleck, et al. "Enzymatic catalysis and dynamics in low–water environments," *Proc NAtl Acad Sci* 89:1100–04 (1992).
Arnold, "Engineering enzymes for non–aqueous solvents," *TIBTECH* 8:244–49 (1990).
Baker, "Effects of the presence of water on lysozyme conformation," *Biopolymers* 22:1637–40 (1983).
Braco, et al., "Production of abiotic receptors by molecular imprinting of proteins," *Proc Natl Acad Sci* 87:274–77 (1990).
Brink, et al., "Biocatalysis in organic media," *Enzyme Microb Technol* 10:736–43 (1988).
Brown, et al. eds., *Chemistry: The Central Science* Fifth Edition (Prentice Hall, Englewood Cliffs, NJ).
Burke, et al., "Determination of organic acids in seven wheat varieties by capillary gas chromatography," *Analytical Biochemistry* 149:421–29 (1985).
Cambou & Klibanov, "Comparison of different strategies for the lipase–catalyzed preparative resolution of racemic acids and alcohols: Asymmetric hydrolysis, esterification, and transesterification," *Biotechnology and Bioengineering* XXVI:1449–54 (1984).
Dabulis & Klibanov, "Molecular imprinting of proteins and other macromolecules resulting in new adsorbents," *Biotechnology and Bioengineering* 39:176–85 (1992).
Dordick, "Enzymatic catalysis in monophasic organic solvents," *Enzyme Microb Technol* 11:194–211 (1989).
Dordick, "Patents and Literature. Biocatalysis in Nonaqueous Media," *Applied Biochemistry and Biotechnology* 19:103–13 (1988).
Ebbing & Wrighton, eds., *General Chemistry* Second Edition, (Houghton Mifflin Co, Boston).
Gupta, "Enzyme function in organic solvents," *Eur J Biochem* 203:25–32 (1992).
Hellman, et al., "The effect of freeze–drying on the quaternary structure of L–asparaginase from *Erwinia Carotovora*," *Biochimica et Biophysica Acta* 749:133–42 (1983).
Inaba, et al., "Application of polyethyleneglycol–modified enzymes in biotechnological processes: organic solvent–soluble enzymes," *TIBTECH* (1986).
Khmelnitsky, et al., "Engineering biocatalytic systems in organic media with low water content," *Enzyme Microb Technol.* 10:710–24 (1988).
Kise, et al., "Protease–catalyzed synthetic reactions and immobilization–activation of the enzymes in hydrophilic organic solvents," *J Biotechnol* 14:239–54 (1990).
Klibanov & Ahern, "Thermal stability of proteins," *Protein Engineering*, Oxender & Fox, eds., pp213–218 (Alan R. Liss, Inc. 1987).
Klibanov, "Asymmetric transformations catalyzed by enzymes in organic solvents," *Acc Chem Res* 24(4):114–120 (1990).

(List continued on next page.)

Primary Examiner—Sean McGarry
Assistant Examiner—Mary Schmidt
(74) *Attorney, Agent, or Firm*—Holland & Knight LLP

(57) ABSTRACT

Methods and formulations for delivery of macromolecules, such as proteins, polysaccharides, and nucleic acids, are disclosed, where the macromolecule is dissolved or dispersed in a low toxicity organic solvent which can be aerosolized for delivery to a patient's lungs by inhalation. Optionally, appropriate solubility enhancers are also present in the formulations composition.

11 Claims, No Drawings

OTHER PUBLICATIONS

Klibanov, "Enzymatic production of chemicals in organic solvents," *Biocatalysis in Inorganic Media* Proceedings of an International Symposium held at Wageningen, The Netherlands, pp. 115–16 (1987).

Klibanov, "Enzymes that work in organic solvents," *Chemtech* 354–359 (1986).

Laitinen & Harris, *Chemical Analysis: An advanced text and reference* (McGraw–Hill Book Company).

Lee & Timasheff, "The stabilization of proteins by sucrose," *J Biol Chem* 256(14):7193–7201 (1981).

Lide, ed., *CRC Handbook of Chemistry and Physics* (72nd Ed. 1991–1992), pp 15–43 to 15–50 (CRC Press, Boston 1991).

Makita, et al., "Lipase catalyzed synthesis of macrocyclic lactones in organic solvents," *Tetrahedral Letters* 28(7):805–808 (1987).

Mozhaev, et al., "Catalytic activity and denaturation of enzymes in water/organic cosolvent mixtures α-Chymotrypsin and laccase in mixed water/alcohol, water/glycol and water/formamide solvents," *Eur J Biochem* 184:597–602 (1989).

Norin, et al., "Lipase immobilized by adsorption," *Appl Microbiol Biotechnol* 28:527–30 (1988).

Poole & Finney, "Hydration–induced conformational and flexibility changes in lysozyme at low water content," *Int J Biol Macromol* 5:308–10 (1983).

Riva, et al., "Protease–catalyzed regioselective esterification of sugars and related compounds in anhydrous dimethylformamide," *J Am Chem Soc* 110:584–89 (1988).

Rupley, et al., "Water and globular proteins," *TIBS* 18–22 (1983).

Russell & Klibanov, "Inhibitor–induced enzyme activation in organic solvents," *J Biol Chem* 263(24):11624–26 (1988).

Ryu, "How do organic solvents affect peroxidase structure and function?" *Biochem* 31:2588–98 (1992).

Schulze & Klibanov, "Inactivation and stabilization of subtilisins in neat organic solvents," *Biotechnology and Bioengineering* 38:1001–06 (1991).

Stahl, et al., "Induced stereoselective and substrate selectivity of bio–imprinted a–chymotrypsin in anhydrous organic media," *J Am Chem Soc* 111:9366–68 (1991).

Stahl, et al., "The synthesis of a D–amino acid ester in an organic media with –chymotrypsin modified by a bio–imprinting procedure," *Biotechnology Letters* 12(3):161–66 (1990).

Stryer, *Biochemistry*, 3rd ed. pp 7–10, 29, 77, 186 (W.H. Freeman & Co. New York 1988).

Tawaki & Klibanov, "Inversion of enzyme enantioselectivity mediated by the solvent," *J. Am Chem Soc.* 114(5):1882–84 (1992).

Wedzicha, et al., "Effect of surfactants and dispersed components on the activity and reactivity of sorbic acid," *Food Additivies and Contaminatns* 7(5):695–709 (1990).

Zaks & Klibanov, "Enzymatic catalysis in nonaqueous solvents," *J Biol Chem* 263(7):3194–3201 (1988).

Zaks & Klibanov, "Enzyme catalyzed processed in organic solvents," *Proc Natl Acad Sci* 82:3192–96 (1985).

Zaks & Klibanov, "the effect of water on enzyme action in organic media," *J Biol Chem* 263:8017–21 (1988).

Zaks & Russell, "Enzymes in organic solvents: properties and applications," *J Biotechnol* 8:259–270 (1988).

Bromberg & Klibanov, "Transport of proteins dissolved in organic solvents across biomimetic membranes," *Proc Natl Acad Sci U S A.* 92(5):1262–6 (1995).

Chin, et al., "On protein solubility in organic solvents," *Biotechnology and Bioengineering* 44:140–45 (1994).

Patton, et al., "Breathing Life into Protein Drugs", *Nature Biotechnology* 16:141–143 (1998).

Shugar, "The measurement of lysozyme activity and the ultra–violet inactivation of lysozyme," *Biochim. Biophys. Acta* 8:302–9 (1952).

U. S. Federal Register vol. 62, No. 85, pp. 24301–24309, 1998.

* cited by examiner

NONAQUEOUS SOLUTIONS AND SUSPENSIONS OF MACROMOLECULES FOR PULMONARY DELIVERY

CROSS-REFERENCE TO RELATED APPLICATIONS

This application claims benefit of Provisional Application Ser. No. 60/109,254 filed Nov. 19, 1998 and Provisional Application Ser. No. 60/116,860 filed Jan. 22, 1999.

STATEMENT REGARDING FEDERALLY FUNDED RESEARCH

The Federal Government has certain rights in the invention disclosed herein by virtue of Grant No. 62063 to Alexander Klibanov from the National Science Foundation.

FIELD OF THE INVENTION

The present invention is in the field of pulmonary delivery of bioactive molecules.

BACKGROUND OF THE INVENTION

Due to their large size, most macromolecules are delivered by injection, and noninvasive delivery systems usually do not work. Although some digestion resistant small peptides, such as 1-desamino-8-D-arginine vasopressin (DDAVP; a nine amino acid vasopressin analog) and cyclosporine (11 amino acids), have been delivered successfully by an oral route, proteins or peptides are usually degraded by enzymes in the stomach or intestine. The skin offers an even less naturally permeable boundary to macromolecules than the gastrointestinal tract, and passive transdermal delivery of proteins and peptides using "patch" technology has had limited success.

Drug delivery by inhalation represents a well established mode of administration of low molecular weight pharmaceuticals for various lung disorders, with a promise for noninvasive systemic delivery of drugs in general. Several biopharmaceutical companies are developing methods for pulmonary delivery of peptides and proteins, with one such product already in clinical use (the enzyme DNAse produced by Genentech for the treatment of symptoms of cystic fibrosis in children).

The lung is an attractive target for noninvasive delivery of proteins. Many proteins readily and naturally absorb through the deep lung into the bloodstream. The expanded deep lung of an adult human has a large surface area of about 100 m$^2$ with a potential for high bioavailability. In addition, the lung is a robust organ which, for instance, can successfully cope with at least 10 mg of nuisance dusts in the workplace each day for years. Furthermore, there is no evidence that inhaling autologous proteins presents significant immune issues.

A number of pharmaceutical preparations for pulmonary delivery of drugs has been developed. For example, U.S. Pat. No. 5,230,884 to Evans et al., discloses the use of reverse micelles for pulmonary delivery of proteins and peptides. Reverse micelles are formed by adding a little water to a nonpolar solvent (e.g. hexane) to form microdroplets. In this medium, a surfactant (detergent) will orient itself with its polar heads inward, so that they are in contact with the water and the hydrophobic tails outward. Thus the tiny droplets of water are surrounded by surfactant. The protein to be delivered is dissolved in the aqueous phase.

U.S. Pat. No. 5,654,007 to Johnson et al., discloses methods for making an agglomerate composition containing a medicament powder (e.g. proteins, nucleic acids, peptides, etc.) wherein a nonaqueous solvent binding liquid (a fluorocarbon) is used to bind the fine particles into aggregated units. The agglomerate composition has a mean size ranging from 50 to 600 microns and is allegedly useful in pulmonary drug delivery by inhalation.

PCT/US97/08895 by Massachusetts Institute of Technology discloses particles made of a biodegradable material or drug, which have a tap density less than 0.4 g/cm$^3$ and a mean diameter between 5 $\mu$m and 30 $\mu$m.

PCT/EP97/01560 by Glaxo Group Limited discloses spherical hollow drug particulates for use in pulmonary delivery.

At present, clinically approved systems for pulmonary delivery of biomacromolecules are limited to using either dry powders or aqueous solutions; which are aerosolized, and the resultant "mist" is inhaled by a patient. These approaches, while feasible, may suffer from serious drawbacks. See a review in *Nature Biotechnology* 16, 141–143 (1998) for a more detailed discussion. For example, the problems with powders include their hygroscopicity, clump formation, and irreproducibility. Aqueous solutions of proteins and nucleic acids are free of these shortcomings but are difficult to aerosolize (due to the high boiling point of water) and susceptible to microbial attack.

It is therefore an object of the present invention to provide a minimally invasive delivery method for bioactive agents.

It is another object of the present invention to provide a means for pulmonary delivery of bioactive agents.

SUMMARY OF THE INVENTION

Methods and formulations for delivery of macromolecules, such as proteins, polysaccharides, and nucleic acids, are disclosed, where the macromolecule is dissolved or dispersed in a low toxicity organic solvent which can be aerosolized for delivery to a patient's lungs by inhalation. Optionally, appropriate solubility enhancers are also present in the formulations composition.

DETAILED DESCRIPTION OF THE INVENTION

Definitions

The term low toxicity as used herein refers to a solvent that does not cause permanent long term damage to body cells or organs.

The term aerosol as used herein refers to any preparation of a fine mist of particles, typically less than 10 microns in diameter, which can be in solution or a suspension, whether or not it is produced using a propellant. Aerosols can be produced using standard techniques, such as ultrasonication or high pressure treatment]

The terms solution or dissolve as used herein refer to compositions in which the bioactive agent is present as a monomolecular dispersion. Concentration ranges are from 0 to 500 mg/ml.

Residual solvents in pharmaceuticals are organic volatile chemicals that are used or produced in the syntheses of drug substances, or excipients, or in the preparation of drug products which are not completely removed by processing.

Biocompatible refers to Class 3 residual solvents that do not cause any long term harmful effects on bodily tissues or cells. This is defined in the U.S. Federal Register vol. 62, number 85, pages 24301–24309 as solvents with low toxic potential to man; no health based exposure limit is needed. Class 3 solvents have PDE's of 50 mg or more per day.

As used herein, the term "surfactant" refers to any agent which preferentially adsorbs to an interface between two immiscible phases, such as the interface between water and an organic polymer solution, a water/air interface or organic solvent/air interface.

1. Compositions

Active Ingredients

The formulations disclosed herein can be used for the delivery of a variety of molecules, especially macromolecules. Smaller molecules can also be delivered as well. Macromolecules are generally defined as molecules having a molecular weight of greater than about 1000 daltons. Examples of macromolecules include proteins and large peptides, polysaccharides and oligosaccharides, and DNA and RNA nucleic acid molecules and their analogs having therapeutic, prophylactic or diagnostic activities. Nucleic acid molecules include genes, antisense molecules that bind to complementary DNA to inhibit transcription, and ribozymes. The agents to be incorporated can have any of a variety of biological activities, being, for example vasoactive agents, neuroactive agents, hormones, anticoagulants, immunomodulating agents, cytotoxic agents, prophylactic agents, antibiotics, antivirals, antisense, antigens, or antibodies.

Proteins are defined as consisting of 100 amino acid residues or more; peptides are less than 100 amino acid residues. Unless otherwise stated, the term protein refers to both proteins and peptides as well as peptidomimetic compounds (i.e. peptide-like substances having some non-peptide groups). Examples of proteins include insulin and other hormones. An example of an polysaccharide is heparin.

The formulations may include an active ingredient for local delivery within the lung, or for systemic treatment. For example, formulations for local delivery may be used to treat asthma, emphysema or cystic fibrosis. Representative agents include genes encoding enzymes to treat cystic fibrosis and beta agonists for treatment of asthma. Agents having systemic effects include, but are not limited to, insulin, calcitonin, human growth hormone, erythropoietin ("EPO"), DNAse, leuprolide (or gonadotropin-releasing hormone ("LHRH")), granulocyte colony-stimulating factor ("G-CSF"), parathyroid hormone-related peptide, somatostatin, testosterone, progesterone, estradiol, nicotine, fentanyl, norethisterone, clonidine, scopolomine, salicylate, cromolyn sodium, salmeterol, formeterol, albuterol, and valium.

Solvents

The solvents useful in the compositions are low toxicity organic (i.e. nonaqueous) class 3 residual solvents, such as ethanol, acetone, ethyl acetate, tetrahydofuran, ethyl ether, and propanol. The solvent is selected based on its ability to readily aerosolize the composition. The solvent should not detrimentally react with the active ingredient. An appropriate solvent should be used that dissolves the active ingredient or forms a suspension of the active ingredient. A suspension is also referred to as a dispersion herein.

The solvent moreover should be sufficiently volatile to enable formation of an aerosol of the solution or suspension. Additional solvents or aerosolizing agents, such as freons, can be added as desired to increase the volatility of the solution or suspension.

Concentration

Macromolecules, such as proteins and nucleic acids can be dissolved in some organic solvents, e.g. in ethanol, at relatively high concentrations provided that certain critical guidelines are followed. For example, the protein is preferably lyophilized from an aqueous solution having a pH different, preferably remote, from the isoelectric point of the protein. See Bromberg & Klibanov, *Proc. Natl. Acad. Sci. USA,* 92, 1262–1266 (1995), the disclosure of which is incorporated herein by reference. The solubility of macromolecules in organic solvents can be enhanced by certain additives, such as some inorganic salts, detergents, and water soluble polymers such as poly(ethylene glycol) and carboxymethylcellulose. Alternatively, biomacromolecular dispersions or suspensions in the form of microcrystals or lyophilized powders suspended in organic solvents can be used to make aerosols for pulmonary delivery. Proteins are usually not irreversibly damaged in such systems. The advantages of the nonaqueous formulations for pulmonary delivery include stability against microbial contamination and a greater (compared to water) ease of the aerosol formation due to their volatility.

Preferably the active ingredient is dissolved or dispersed to a concentration of between 0 and 500 mg/ml, more preferably between 1 mg/ml and 100 mg/ml, and most preferably between 10 $\mu$g/ml and 10 mg/ml. The same concentrations can be used as have been used for aqueous solutions delivered via the pulmonary route. The concentration will be determined by the solubility or dispersibility of the macromolecule and the amount of solution or dispersion that can be safely administered. The concentration is also limited by the fact that the solution or suspension needs to be aerosolized. Desired dosages are known for many macromolecules and can be determined by means known to those skilled in the art. Many protein and peptide drugs require deep lung delivery of two to 20 mg per dose. Patton et al., "Breathing Life into Protein Drugs", *Nature Biotechnology* 16:141–143 (February 1998). Since the volume of drug containing solution or suspension delivered to the patient is preferably about 1 to 5 ml, the concentration will preferably be from about 0.4 to 20 mg per ml.

Surfactants and Other Ingredients

The formulations may optionally include a surfactant to enhance solubility or absorption. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

Synthetic or naturally occurring surfactants known in the art, can be used. Surfactants which can be included in the formulation to improve their aerosolization properties include phosphoglycerides. Exemplary phosphoglycerides include phosphatidylcholines, such as the naturally occurring surfactant, L-$\alpha$-phosphatidylcholine dipalmitoyl ("DPPC"). The use of surfactants endogenous to the lung may avoid the need for the use of non-physiologic surfactants. Other exemplary surfactants include diphosphatidyl glycerol (DPPG); sodium dodecyl sulfate (SDS), derivatives of polyethylene glycol (PEG); polyoxyethylene-9-lauryl ether; a surface active fatty acid, such as palmitic acid or oleic acid; sorbitan trioleate (Span 85); glycocholate; surfactin; poloxomers; sorbitan fatty acid esters such as sorbitan trioleate; tyloxapol and a phospholipid; and alkylated sugars such as octyl glucoside. These are added to the solution or dispersion to a concentration above the surfactant's critical micelle concentration (CMC). Concentrations will typically be between 0.001% and 10%.

The surfactant can also be used as a particle stabilizer for suspensions. Other additives, such as some inorganic salts (10 mM to 5 M), and viscosity modifying agents such as the water soluble polymers poly(ethylene glycol) and carboxymethylcellulose (0.1% to 10% (w/v)), may also be used to enhance solubility, stability or absorption.

2. Methods for Making the Compositions

The compositions are made by mixing the macromolecule to be delivered with a suitable biocompatible organic solvent to form a solution or dispersion of the macromolecule. Additional ingredients, such as surfactants and other excipients, both optional, can be added as desired, to improve solubility and delivery, for example. The solvent is selected as described above. Preferably, the macromolecule is lyophilized from an aqueous solution that has a pH different from the pI of the macromolecule, before being dissolved or dispersed in the solvent.

3. Methods for Using the Compositions

The compositions can be delivered by any method and/or device which is currently used for pulmonary delivery. For example, nebulizer can be used. Nebulizers create a fine mist from a solution or suspension, which is inhaled by the patient. The devices described in U.S. Pat. No. 5,709,202 to Lloyd, et al., can be used. A metered dose inhaler (MDI) can also be used. An MDI typically includes a pressurized canister having a meter valve, wherein the canister is filled with the solution or suspension and a propellant. The solvent itself may function as the propellant, or the composition may be combined with a propellant, such as freon. The composition is a fine mist when released from the canister due to the release in pressure. The propellant and solvent may wholly or partially evaporate due to the decrease in pressure.

The present invention is further described by the following non-limiting example.

EXAMPLE

Aerosolization of Lysozyme

Nine mL of ethanol containing 0.1 mg/ml hen egg-white lysozyme (a model protein) was placed in a compressor nebulizer. The reservoir containing the ethanol solution was connected via a plastic tube to a collecting test tube placed in an ice booth to facilitate condensation of the solution. The nebulization was started and continued for 5 minutes. As a result, about one mL of the ethanol solution was collected in the test tube (i.e. was aerosolized). No solution was collected with the nebulizer switched off. The lysozyme activity of the nebulized solution was measured using the standard assay against dried calls of *M. lysodeikticus*. (Shugar, *Biochim. Biophys. Acta* 8, 302 (1952)). The specific activity of the nebulized solution was the same, (±10%) as that of the initial enzyme solution. Therefore, not only was lysozyme aerosolized from an ethanol solution, but in the course of this aerosolization it did not suffer any appreciable loss in enzymatic activity. The same study was repeated using lysozyme dispersions in ethanol at 1 mg/ml and 10 mg/ml with similar results: no appreciable loss of enzymatic activity. Therefore, both the aerosolization and the lack of inactivation upon the active agent have now been demonstrated not only for lysozyme solutions in ethanol but for suspensions as well.

Publications cited herein and the material for which they are cited are specifically incorporated by reference. Modifications and variations of the present invention will be obvious to those skilled in the art from the foregoing detailed description and are intended to be encompassed by the following claims.

What is claimed is:

1. A formulation for pulmonary delivery of a bioactive agent comprising a solution or suspension of a bioactive agent to be delivered in a biocompatible organic solvent suitable for aerosolization of the bioactive molecule, wherein the solvent is a class 3 residual solvent.

2. The formulation of claim 1 wherein the bioactive agent is a therapeutic, diagnostic or prophylactic agent.

3. The composition of claim 1 wherein the bioactive agent is a macromolecule selected from the group consisting of proteins, peptides, polysaccharides, oligosaccharides, and nucleic acid molecules.

4. The formulation of claim 2 wherein the biological agent is selected from the group consisting of vasoactive agents, neuroactive agents, hormones, anticoagulants, immunomodulating agents, cytotoxic agents, prophylactic agents, antibiotics, antivirals, antisense, antigens, and antibodies.

5. The formulation of claim 1 wherein the bioactive agent is for the treatment of a pulmonary disease or disorder.

6. The formulation of claim 1 wherein the bioactive agent is selected from the group consisting of insulin, calcitonin, human growth hormone, EPO, DNAse, gonadotropin-releasing hormone, granulocyte colony-stimulating factor, parathyroid hormone-related peptide, somatostatin, testosterone, progesterone, estradiol, nicotine, fentanyl, norethisterone, clonidine, scopolamine, salicylate, cromolyn sodium, salmeterol, formeterol, albuterol, and valium.

7. The formulation of claim 1 wherein the solvent is selected from the group consisting of ethanol, acetone, ethyl acetate, tetrahydofuran, ethyl ether, and propanol.

8. The formulation of claim 1 wherein the bioactive agent is present in solution or suspension at a concentration up to about 500 mg/ml.

9. The formulation of claim 8 wherein the bioactive agent is present as a suspension.

10. The formulation of claim 1 further comprising an agent selected from the group consisting of surfactants which enhance solubility of the bioactive agent, inorganic salts and viscosity modifying agents.

11. A method of delivery of a bioactive agent comprising administering to a patient an aerosol formulation of a solution or suspension of the bioactive agent in a biocompatible organic solvent, wherein the solvent is a class 3 residual.

* * * * *